United States Patent
Hageman et al.

(10) Patent No.: US 6,471,977 B1
(45) Date of Patent: Oct. 29, 2002

(54) AQUEOUS PROLONGED RELEASE FORMULATION

(76) Inventors: Michael John Hageman, 5262 S. 12th, Kalamazoo, MI (US) 49009; Margaret Luise Possert, 976 S. 4th, Kalamazoo, MI (US) 49009

(*) Notice: Subject to any disclaimer, the term of this patent is extended or adjusted under 35 U.S.C. 154(b) by 0 days.

(21) Appl. No.: 08/696,985

(22) PCT Filed: Jan. 9, 1995

(86) PCT No.: PCT/US95/00023

§ 371 (c)(1),
(2), (4) Date: Aug. 2, 1996

(87) PCT Pub. No.: WO95/19787

PCT Pub. Date: Jul. 27, 1995

Related U.S. Application Data

(63) Continuation of application No. 08/186,572, filed on Jan. 25, 1994, now abandoned.

(51) Int. Cl.[7] .............................................. A61K 38/27
(52) U.S. Cl. ........................ 424/422; 424/426; 424/438; 514/12; 514/21; 530/399
(58) Field of Search ................................. 424/422, 426, 424/438; 514/12, 21; 530/399

(56) References Cited

U.S. PATENT DOCUMENTS

| | | | |
|---|---|---|---|
| 4,118,380 A | 10/1978 | Immer et al. ............ 260/112.5 |
| 4,774,091 A | 9/1988 | Yamahira et al. ............ 424/426 |
| 4,816,568 A | 3/1989 | Hamilton et al. ............ 530/399 |
| 4,857,506 A | 8/1989 | Tyle ............................. 514/12 |
| 4,863,736 A | 9/1989 | Azain et al. ................ 424/423 |
| 4,888,416 A | 12/1989 | Janski et al. ................ 530/399 |
| 4,977,140 A | 12/1990 | Ferguson ..................... 514/12 |
| 4,985,404 A | 1/1991 | Mitchell ........................ 514/6 |
| 5,013,713 A | 5/1991 | Mitchell ........................ 514/2 |
| 5,015,627 A | 5/1991 | Lindsey et al. ................ 514/12 |
| 5,021,241 A | 6/1991 | Yamahira et al. ............ 424/426 |
| 5,169,834 A | 12/1992 | Arendt ........................... 514/8 |
| 5,198,422 A | 3/1993 | Clark et al. .................... 514/12 |

FOREIGN PATENT DOCUMENTS

| | | | |
|---|---|---|---|
| AU | 8655983 | 4/1986 | |
| EP | 140 255 | 5/1985 | ............ A61K/9/00 |
| EP | 0 193 917 | 9/1986 | ............ A61K/9/18 |
| EP | 0 211 601 | 2/1987 | .......... A61K/37/36 |
| EP | 0 353 045 | 1/1990 | .......... A61K/37/36 |
| EP | 0 374 120 | 6/1990 | .......... A61K/47/10 |
| ZA | 912239 | 3/1991 | |

OTHER PUBLICATIONS

Machlin, L.J., *J. Dairy Sci.*, vol. 56, No. 5, 575–580 (1972).
Hutton, J.B., *J. Endocrin.*, 16, 115–125 (1957).
Hageman et al., *J. Agric. Food Chem.*, 40(2), 348 (1992).
Bourne et al., *J. Dairy Sci.*, vol. 60:1629–1635 (1977).
Pitt, *Int. J. Pharmaceutics*, 59:173–196 (1990).
Dalke, B.S. et al., "Dose–Response Effects of Recombinant Bovine Somatotropin Implants ofn Feedlot Performance in Steers," J. Animal Science, 70(4):2130–37 (1992).
Wagner, J.F. et al., "Effect of Growth Hormone (GH) and Estradiol (E2β) Alone and in Combination on Beef Steer Growth Performance, Carcass and Plasma Constituents," Abstract 159 of Animal Sciences vol. 66 (1988).

*Primary Examiner*—Gollamudi S. Kishore
(74) *Attorney, Agent, or Firm*—Marshall, Gerstein & Borun

(57) ABSTRACT

Prolonged parenteral release into the circulatory system of a cow of a bioactive bovine somatotropin at desirably effective levels can be achieved using novel compositions in which the bovine somatotropin is present it an aqueous liquid at a dose of at least about 150 mg and at a concentration of at least about 50 mg/ml. The aqueous bovine somatotropin formulation provides for the sustained release of bovine somatotropin into the circulatory system of the animal for greater than three (3) days.

21 Claims, 2 Drawing Sheets

AQUEOUS PROLONGED RELEASE FORMULATION

This application is the national phase of international PCT/US95/00023, which is a continuation of U.S. Ser. No. 08/186,572, filed Jan. 1994, now abandoned.

BACKGROUND OF THE INVENTION

This invention relates to novel compositions useful for the sustained-release of bioactive proteins. More particularly, the present invention provides a superior aqueous sustained release injectable formulation of bovine somatotropin. Also provided are methods of using these novel compositions for the sustained or prolonged release of bovine somatotropin.

With the advent of genetic engineering, the large-scale availability of many bioactive peptides and proteins has been achieved. However, the administration of these recombinantly produced peptides and proteins presents a unique set of problems. In many cases the maintenance of the biological effect of these proteins requires long-term administration. Since daily administration of these agents is inconvenient, sustained or prolonged release is preferred.

For numerous reasons, the art has long focused on the use of biocompatible oils as vehicles to achieve the sustained release of many drugs, including proteins and specifically somatotropins. Among the patents directed to this technology are U.S. Pat. No. 5,013,713 to Mitchell and U.S. Pat. No. 4,977,140 to Ferguson et al. Mitchell reports that prolonged parenteral release of bovine somatotropin (bSt;BGH) at desirably effective levels can be achieved using substantially non-aqueous compositions comprising at least about 10% by weight of a biologically active somatotropin and, as a continuous phase of the composition, a biocompatible oil such as corn oil. Ferguson et al. report that the injection of a sustained release formulation comprising bSt, wax and an oil increases daily milk production in a cow for an extended period of time.

The above patents illustrate the art's emphasis on the use of non-aqueous delivery systems for the prolonged release of somatotropins. Noticeably absent from the art is the use of an aqueous formulation to achieve the prolonged release of bSt. Among the reasons the art has avoided using aqueous systems for the sustained delivery of proteins, especially somatotropins, is the general view that proteins are highly unstable when exposed to aqueous environments for long periods of time. (Pitt, Int. J. Pharmaceutics 59:173–196 (1990)). It is also generally thought that one could not obtain prolonged release of proteins or peptides using an aqueous formulation without making some effort to alter the solubility of the molecule or alter absorption of the molecule by, for example, absorption modifiers and viscosity inducing agents. Even when oils are used, Mitchell reports that antihydration agents are often added to a delivery system for bioactive proteins, or the protein is complexed with metals or metal compounds, to modify the release of the protein into an animal's bloodstream. Use of these absorption modifying agents, however, alter protein solubility or induce viscosity and can diminish convenient injectability of a composition and/or lead to significant tissue irritation at the injection site.

While it is difficult to determine the origin of the art's bias against the use of aqueous formulations to achieve the prolonged release of proteins such as bSt, it may be based upon research performed by J.B. Hutton (J. Endocrin. (1957) 16, 115–125). In his research, Hutton studied the effect of subcutaneous injections of graded doses (6.25, 12.5, 25.0, 50.0, 100.0 and 200.0 mg) of bovine growth hormone (bSt) dissolved in 5 ml saline (concentrations of 1.25, 2.5, 5, 10, 20 and 40 mg/ml, respectively) on the yield and composition of cow's milk. The primary parameter studied by Hutton was an increase in milk yield. Hutton reported that mean milk yield over a four day period was influenced by the dose of bSt administered. Hutton did not present any data, however, that the higher milk yield was sustained over the entire four day period. Hutton asserted that a single 50 mg (10 mg/ml) bSt injection would provide enhanced milk yield for four days. Hutton acknowledged, however, that this assertion was based upon calculations requiring certain assumptions. The nature of these assumptions was not disclosed nor was any supporting data provided regarding his assertions. Hutton also did not present any data regarding the impact of the graded bSt doses on bSt serum levels or to indicate that higher doses of bSt administered in higher concentrations can effect the sustained release of bSt into the circulatory system of a cow.

An opportunity for the art to overcome its bias against the use of aqueous formulations to achieve the prolonged release of bSt occurred when L. J. Machlin, building upon the work of Hutton and others, investigated the effects of high potency bSt preparations relatively free of thyrotrophin (TSH) and prolactin contamination on milk production in cows (J. Dairy Sci. (1972) Vol. 56, No. 5, 575–580). Machlin found that injection of bSt every third day (60 mg dose, unknown concentration, three injections total) improved milk production as much as the same total dose given daily (20 mg dose, unknown concentration, nine daily injections). Machlin did not consider, however, whether use of aqueous high potency bSt preparations would result in the sustained release of the growth hormone into the circulatory system of a cow. In fact, Machlin states that "[t]he half-life of BGH is 19-20 minutes in Holstein cows. Therefore, even with some delay in absorption from the subcutaneous site of injection, an increase in plasma BGH over endogenous levels could not be expected more than 12 hours past injection. Thus a prolonged increase in circulating BGH probably does not account for the effect." Machlin also did not recognize the interrelationship between the dose and concentration of bSt in effecting sustained release of bSt from an aqueous formulation.

In order to better understand Machlin's observations, Bourne et al., J. Dairy Sci. Vol. 60:1629-1635 (1977), undertook measurement of serum bSt levels following subcutaneous injection of similar doses, Bourne et al. observed that average serum bSt concentrations reached a maximum one to three hours after injection and returned to pre-injection concentrations within twenty-four hours. This data by Bourne et al. argues against the sustained release of BGH into the bovine circulatory system beyond 24 hours and is consistent with the suggestion by Machlin that an increase in plasma BGH over endogenous levels could not be expected more than 12 hours past injection.

Subsequent to the studies of Hutton, Machlin and Bourne et al., the art focused away from their work. Numerous investigators used aqueous solutions for daily regimens with bSt concentrations generally ranging from the 1–10 mg/ml and a dose of 5–45 mg. However, none of the cases reported any significant bSt serum levels exceeding 48–60 hours. Therefore, the art continued to assume that aqueous formulations were inappropriate vehicles for achieving the prolonged release of bSt into the circulatory system of a cow.

The present invention overcomes this misconception by the art and provides a sustained release aqueous injectable formulation of bSt and methods of using this formulation to achieve the sustained or prolonged release of bSt into the circulatory system of an animal.

INFORMATION DISCLOSURE

Machlin, L. J. (*J. Dairy Sci.* (1972) Vol. 56, No. 5, 575–580). Machlin reports that, over a nine day period, injection of bovine growth hormone every third day (60 mg dose, 180 mg total) improves milk production as much as the same total dose given daily (20 mg dose, 180 mg total). Machlin reports, however, that "[t]the half-life of BGH is 19–20 minutes in Holstein cows. Therefore, even with some delay in 30 absorption from the subcutaneous site of injection, an increase in plasma BGH over endogenous levels could not be expected more than 12 hours past injection." Further, Machlin does not consider the question of whether aqueous formulations can be used as vehicles for achieving the prolonged release of proteins into the circulatory system of an animal.

Hutton, J. B. (*J. Endocrin.* (1957) 16, 115–125) reports on the effect growth hormone has on the yield and composition of cow's milk. Hutton reported that mean milk yield over a four day period was influenced by the dose of bSt administered. Hutton did not present any data, however, that the higher milk yield was sustained over the entire four day period. Hutton also did not present any data regarding the impact of the graded bSt doses on bSt serum levels or to indicate that higher doses of bSt administered in higher concentrations can effect the sustained release of bSt into the circulatory system of a cow.

Hageman et al., *J. Agric. Food Chem.*, 40(2), 348 (1992) report that the development of sustained-release dosage forms for the efficient delivery of somatotropins is complicated by the instability of the proteins upon exposure to water, especially at physiological conditions of pH 7.4 and 37° C.

Bourne et al., *J. Dairy Sci.*, Vol. 60:1629–1635 (1977), report that average serum bSt levels following subcutaneous injection of 10, 50 and 100 mg doses in 5 ml aqueous media reached a maximum level one to three hours after injection and returned to pre-injection concentrations within twenty-four hours.

Pitt, *Int. J. Pharmaceutics* 59:173–196 (1990), reports on the difficulties in developing parenteral sustained release delivery systems for proteins such as the somatotropins which are highly unstable in aqueous environments at high protein concentrations.

U.S. Pat. No. 5,013,713 to Mitchell issued May 7, 1991, discloses a method for achieving prolonged release of a biologically active somatotropin into the circulatory system of an animal by the parenteral administration to the animal of a substantially non-aqueous composition of at least about 10% by weight of a biologically active somatotropin and, as a continuous phase of the composition, a biocompatible oil. Mitchell emphasizes that his composition should be non-aqueous in order not to accelerate release.

U.S. Pat. No. 4,977,140 to Ferguson et al. issued Dec. 11, 1990, discloses a method for obtaining 28 days of increased daily milk production from a dairy cow by injecting into the cow 2 to 10 grams of a formulation comprising 10–25% bovine somatotropin suspended in a carrier that comprises 8–20% of a wax and 80–92% of an oil. Ferguson et al. do not consider the question of whether aqueous formulations can be used as a prolonged release vehicles.

European Patent Application 0 211 601, published Feb. 25, 1987, discloses animal growth-promoting compositions for administration to animals that comprise a mixture of water, a growth-promoting hormone (e.g., bovine growth hormone) and a polyoxyethylene block copolymer as a stabilizer. Preferred compositions contain 50–99.9 wt. % water, 0.05–10 wt. % growth hormone and 0.05–50 wt. % block copolymer. The reference reports that the presence of the block copolymer in the composition inhibits solids precipitation and loss of activity of the hormone during storage. The copolymers also provide for the sustained release of growth hormone due to their ability to undergo a well-known sol-gel transition when exposed to 37° C. at the injection site; thus providing an in situ formed matrix for slow release of protein.

U.S. Pat. No. 5,169,834 to Arendt (similar to South African Patent 912239) discloses a lyophilized product comprising 81–96.5% w/w biologically active drug (e.g., somatotropin) and a buffer system comprising 0.1–7.6% w/w sodium carbonate and 7.6–15% w/w sodium bicarbonate with the total buffer system concentration not exceeding 15.2% w/w. The formulated powder is reconstituted with saline solution in a small vial to form the desired concentration. The patent describes the utility of the aqueous solutions only in terms of daily administration and makes no indication of potential use for prolonged release of the bioactive drug.

U.S. Pat. No. 4,888,416 to Janski et al. discloses a dried stabilized bioactive protein product coated with a strongly bound ionic detergent. Coating the protein with the ionic detergent reportedly stabilizes the proteins so that they retain their bioactivity and solubility when in contact with body fluid.

European Patent 0 193 917, published Sep. 10, 1986, discloses a biologically active composition having slow release characteristics comprising a water-soluble or-dispersible carbohydrate polymer (e.g., dextran; dextrin; alginate; vegetable gums; or cellulose, or their mixtures) and a biologically active macromolecule such as bovine somatotropin. These aqueous preparations require the use of complexation with carbohydrate polymers to provide sustained blood levels of somatotropins.

U.S. Pat. No. 4,857,506 to Tyle describes an aqueous internal phase containing somatotropin for which sustained release is obtained upon incorporation into a multiple emulsion, i.e. oil/water/oil emulsion.

European Patent 0 353 045, published Jan. 31, 1990, reports the use of aqueous solutions with stabilizers, but sustained release requires their incorporation into a rate controlling device, i.e. osmotic pump/reservoir system. Also mentioned is the potential use of gels, pastes, microspheres, microcapsules, implants and the like as parenteral compositions.

U.S. Pat. No. 4,816,568 to Hamilton et al. entitled "Stabilization of growth hormones," describes the need of various stabilizers for preservation of soluble bioactivity of the growth hormone in aqueous environments, again emphasizing the need for stabilizers.

European Patent 0 374 120, published Jun. 20, 1990, reports that the stabilization of implantable controlled delivery devices containing aqueous solutions can be accomplished by the incorporation of polyol and buffer into the solution, providing no evidence that aqueous solutions without such stabilizers could provide sustained release upon injection.

U.S. Pat. No. 4,118,380 entitled "Decapeptide analogs of somatostatin," reports the necessity of using low solubility salts or pharmaceutically acceptable carriers in aqueous solutions to provide a depot or sustained release effect of the somatostatin.

Australian Patent 8655983 (related to U.S. Pat. Nos. 4,774,091 and 5,021,241) entitled "Slow release preparation of growth promoting or bony metabolism peptide-with collagen, gelatin and/or albumin as carrier protein," discusses the need for a carrier protein to obtain sustained release from protein injections.

European Patent 140 255 (similar to Australian Patent 8655983) entitled "Sustained-release injections," reports that not only is a carrier protein necessary to obtain sustained release from protein injections, but a viscous solvent, unlike water, is also required for suspension of the protein/carrier composition.

SUMMARY OF THE INVENTION

The present invention provides to the art substantially aqueous bovine somatotropin compositions and a method for achieving the prolonged release of a biologically active somatotropin into the circulatory system of an animal by the parenteral administration to the animal, preferably by subcutaneous or intramuscular injection, of the substantially aqueous bovine somatotropin compositions. The compositions comprise at least about 150 mg of a biologically active bovine somatotropin in an aqueous carrier at a concentration of at least about 50 mg/ml. The aqueous bSt formulation provides for the sustained release of bSt into the circulatory system of the animal for greater than about 72 hours.

DETAILED DESCRIPTION

Figure 1:
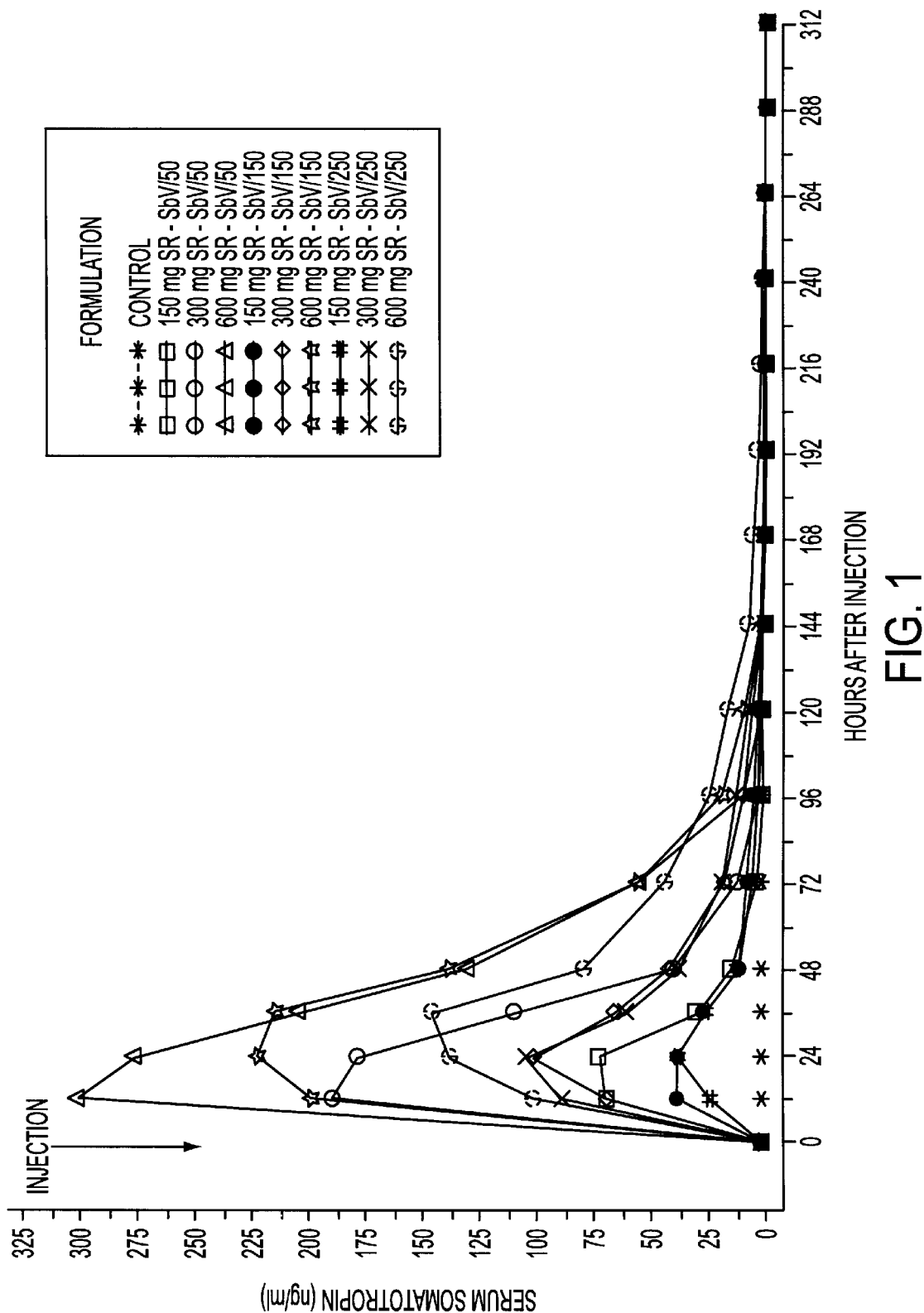
FIG. 1 illustrates the mean serum bSt concentrations over time of the ten bSt treatment groups depicted in Table 1.

Throughout this specification, percentages of compositions are by weight and temperatures are in degrees Celsius unless indicated otherwise.

As used in this specification, the term "biologically active" or "bioactive" polypeptide herein means a polypeptide that, following appropriate parenteral administration to an animal, has a demonstrable effect on a biological process of that animal. The effect may be hormonal, nutritive, therapeutic, prophylactic or otherwise, and may mimic, complement or inhibit a naturally occurring biological process. Although there is an enormous variety of such effects and processes, the stimulation of growth, lactation, egg or offspring production and/or feed efficiency in food animals can be mentioned as exemplary. Other examples include the production of wool, furs or other non-food animal products. Although the polypeptide may be in its active form in compositions of this invention prior to administration to an animal, the term herein also includes polypeptides that develop bioactivity after such administration.

The compositions of the present invention are used for the prolonged release of bovine somatotropin in cattle. Bovine somatotropin is a hormone which is useful for enhancing lean-to-fat ratio, feed efficiency, growth rate and milk production in cattle (e.g., dairy cows). As used herein, the term "bovine somatotropin" means a polypeptide that has biological activity and chemical structure substantially similar to the somatotropin produced in the pituitary gland of a cow. Such bovine somatotropin includes the natural somatotropin produced by bovine pituitary somatotropic cells, and, alternatively, bovine somatotropin expressed by genetically transformed microorganisms such as *E. coli,* other bacteria or yeasts. Such alternatively produced somatotropins may have an amino acid sequence identical to the natural somatotropin or may be analogs having one or more variations in amino acid sequence which may provide enhanced biological activity or some other advantage.

Compositions of this invention contain bovine somatotropin (bSt) at a dose level of at least about 150 mg of a biologically active bSt dissolved in water to a concentration of at least about 50 mg/ml. Higher doses of bSt, e.g., at least about 300 mg, or even 600 mg, of biologically active bSt dissolved in water to a concentration of at least about 50 mg/ml are also desirable. In addition, increasing the concentration above 50 mg/ml is also advantageous for providing prolonged release of the bSt when parenterally injected (as measured in the blood stream of cattle).

Among the characteristics of the compositions of the present invention is that they do not require absorption modifying agents to provide prolonged release of the bioactive polypeptide at biologically effective rates. It has been found that these compositions provide sustained release over a conveniently long period of time, and that such amounts are not so large as to cause inconvenience to the administrator or to the cow. Injection of the claimed compositions into cattle causes extremely low tissue irritation at injection sites as compared to non-aqueous BGH sustained release formulations. Little to no tissue irritation is noted with the aqueous sustained release formulations of the present invention.

As aforesaid, the compositions of this invention are attractively useful for parenteral administration, e.g., by subcutaneous or intramuscular injection. The duration of prolonged release is that period of time during which the polypeptide is delivered at the rate required for the desired biological effect, typically indicated by the concentration of the polypeptide in the animal's circulating blood stream. The period of prolonged release is desirably at least greater than about 72 hours. In other cases, it may be at least about 120 hours, or more desirably for many applications at least about 144 hours.

The bSt can be provided in the form of a powder (e.g., lyophilized or spray dried) which is mixed relatively gently with the aqueous carrier, such as with a propeller agitator or the like. In a preferred embodiment, prior to lyophilization or spray drying, protein stabilizers (e.g., polysorbate 80) and bulking agents (e.g., mannitol), are dissolved in a bSt/water solution. This bSt composition is then gently mixed with water to form the prolonged release compositions of the present invention. Polysorbate 80 is a nonionic surfactant used to stabilize the bovine somatotropin toward interfacial denaturation that can occur during large scale processing or reconstitution. For example, 0.125% w/v polysorbate 80 can be added to the water into which the bovine somatotropin prior to dissolution and lyophilization to protect the somatotropin. Bulking agents like mannitol can facilitate reconstitution. Other formulation excipients, such as buffers (e.g., sodium bicarbonate), or tonicity modifying agents (e.g., sodium chloride) may be added, but are not necessary.

The following specific examples of sustained release formulations according to the present invention are provided to assure that the reader fully understands the invention and how to make its formulations, but do not imply any limitation of the scope of the invention.

EXAMPLE 1

Preparation of Bovine Somatotropin

Bovine somatotropin was prepared and isolated in accordance with WO 35 87/00204, with the final steps of purification/isolation being the dialysis of solutions against very dilute NaOH solutions of pH 9–10.5 and crossflow microfiltration to yield protein solutions ranging from 10-150 mg/ml. These solutions were sterile filtered and were lyophilized to yield bulk powder.

EXAMPLE 2

Preparation of Formulation

Bulk lyophilized somatotropin from Example 1 was dissolved in water, placed into 100 ml vials and lyophilized. Appropriate amounts of water were added to the vials to dissolve the newly lyophilized somatotropin to produce somatotropin solutions having concentrations of either 50, 150 or 250 mg/ml in the vials. These different concentrations of somatotropin were filled into syringes to provide doses of either 150, 300 or 600 mg per syringe (Table 1). Alternatively, one could fill the bulk drug solution from Example 1 directly into vials and avoid the redundant lyophilization step.

EXAMPLE 3

Injection

Non-pregnant, non-lactating Holstein heifers (475kg visually estimated body weight) were housed in dry lots and received 35 kg alfalfa silage per head per day; water was available for ad lib consumption. Heifers were assigned randomly to groups (six per group) to receive the following treatments via subcutaneous injection (SR=sustained release):

1) 150 mg SR-bSt/50, 3.0 ml dose volume;
2) 150 mg SR-bSt/150, 1.0 ml dose volume;
3) 150 mg SR-bSt/250, 0.6 ml dose volume;
4) 300 mg SR-bSt/50, 6.0 ml dose volume;
5) 300 mg SR-bSt/150, 2.0 ml dose volume;
6) 300 mg SR-bSt/250, 1.2 ml dose volume;
7) 600 mg SR-bSt/50, 12.0 ml dose volume;
8) 600 mg SR-bSt/150, 4.0 ml dose volume;
9) 600 mg SR-bSt/250, 2.4 ml dose volume;
10) No injection (control).

All formulations were injected subcutaneously over the rib, caudal to the left shoulder using an 18 gauge by 2.5 cm disposable needle with a 3 to 10 ml disposable syringe, depending on injection volume. Hair at injection site was clipped prior to injection to allow for monitoring of tissue reaction. The injection sites were evaluated once daily for the first 10 days of the study. Injection site monitoring was discontinued when no reactions were observed on any SR-somatotropin injected animals 10 days post-injection.

EXAMPLE 4

Serum Assay

Blood (7 ml) was collected in 10 ml evacuated tubes via the tail vein for 14 days following injection. Injections were given at time 0 and blood samples collected at 0, 12, 24, 36, 48, 72, 96, 120, 144, 168, 192, 216, 240, 264, 288 and 312 h following injection. Blood was allowed to clot at ambient temperature for 1 hour, centrifuged at 1500×g, and the serum decanted and stored at −20° C. All serum samples were assayed for bSt by radioimmunoassay (RIA) following the procedure of G. D. Niswander, et al., *Endocrinol.* 84:1166 (1969).

EXAMPLE 5

Duration of Serum bSt Elevation

Figure 2:
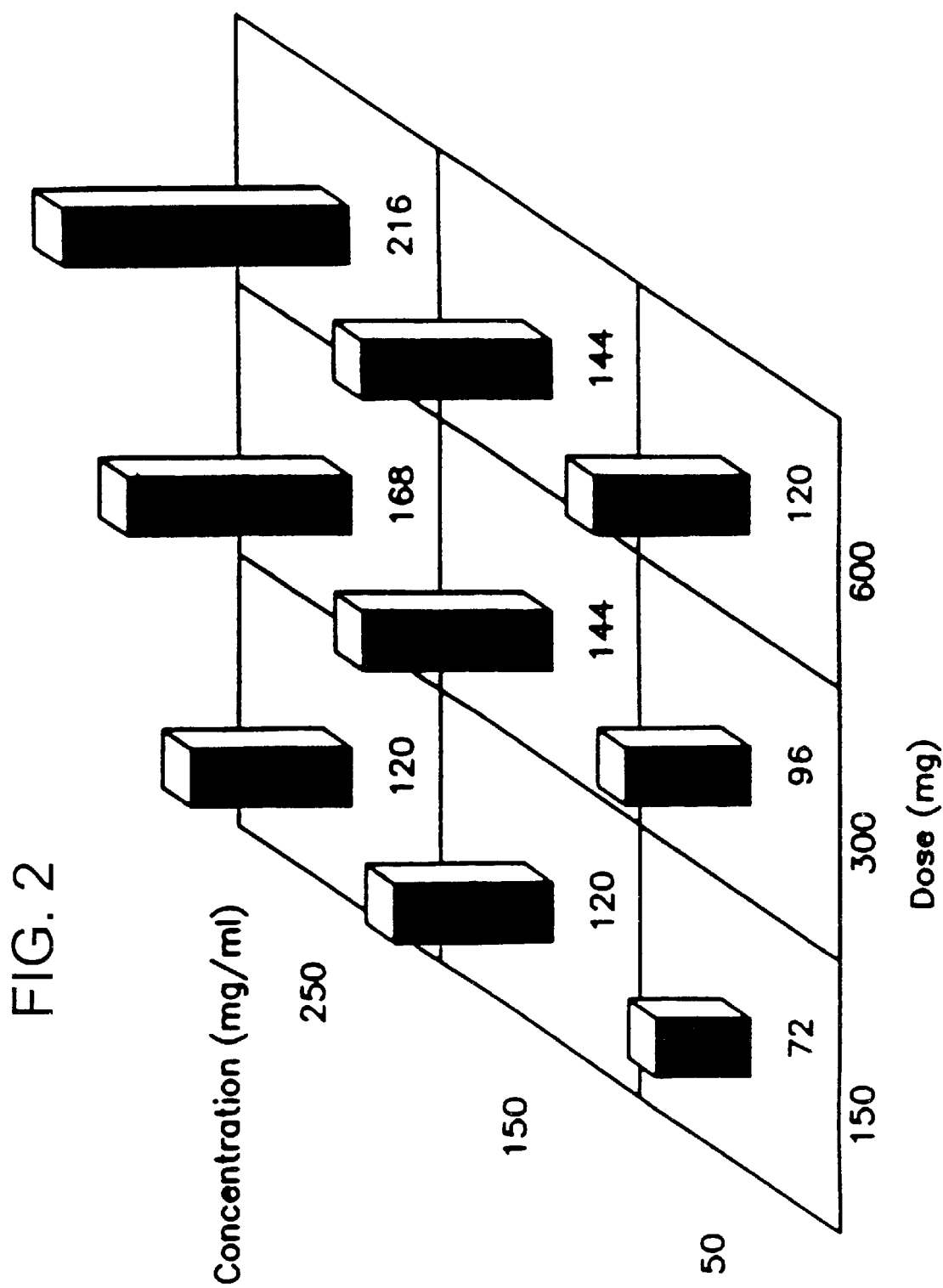
FIG. 2 illustrates the length of time that each of the ten bSt treatment groups depicted in Table 1 were able to elevate serum bSt concentration above that of control heifers.

Mean serum bSt concentrations over time of the ten treatment groups in Table 1 are depicted in FIG. 1. The length of time that each of the various SR-bSt formulations was able to elevate serum bSt concentration above that of control heifers is depicted in FIG. 2. It is apparent that as dose increased within a particular bSt concentration, the number of hours that serum bSt remained elevated above controls also increased (Table 2, FIG. 2). Likewise, as bSt concentration increased from 50 mg bSt/ml to 250 mg bSt/ml within a specific dose, the number of hours serum bSt was elevated above controls also increased (Table 2, FIG. 2). All formulations tested provided elevated mean serum bSt for greater than 72 hours (Table 2, FIG. 2). The lowest dose/concentration combination which was able to elevate mean serum bSt for 144 h was 300 mg SR-bStV150 (Table 2, FIG. 2).

Increasing both dose and concentration (600 mg SR-bSt/250) extended the time serum bSt was elevated to 216 h (Table 2, FIG. 2).

The results indicate that an interaction between dose and concentration resulted in increased duration of bSt elevation (Table 2). Specifically, the effect of increasing both dose and concentration has a greater impact on duration than would be predicted by the additive effect of increasing each one separately. Therefore, the results indicate that there is a synergistic interaction between increasing dose and concentration which results in a greater than expected sustained release of bSt into the circulatory system of the cow.

All combinations of bSt dose and concentration studied (treatment groups 1–9, Table 1) could be used to significantly elevate serum bSt concentration and provide sustained release. Concentrations below 180 mg/ml possessed especially preferred reconstitution, syringeability and injectability characteristics.

While not wishing to be bound by any theory, it is our belief that the sustained release of an aqueous solution of bovine somatotropin (bSt) in vivo is dictated by the competitive processes of decomposition within and dissolution from a "gel-like" bSt depot which forms at the injection site due to the physiological conditions of the cow (pH 7.4 and 39 C). Given this belief, factors such as protein concentration and bSt dose would be expected to dramatically affect duration of serum bSt levels. For example, increasing bSt concentration would allow for smaller injection volume which presumably would lead to faster bSt depot formation and a smaller overall surface area for subsequent dissolution of bSt to occur (i.e., leading to a longer duration). Increasing bSt dose would provide excess bSt to compensate for the decomposition of bSt that may be occurring at the injection site over the duration of bSt release from the site. In effect, the excess would increase the time for which detectable amounts of bSt would continue to be released.

While specific embodiments of the invention have been described, it should be apparent to those skilled in the art that various modifications thereof can be made without departing from the true spirit and scope of the invention. Accordingly, it is intended that the following claims cover all such modifications within the full inventive concept.

TABLE 1

Experimental Design and Formulation Description.

| Formulation[a] | N | Somatotropin Concentration | Dose | Dose Volume |
|---|---|---|---|---|
| SR-bSt/50 | 6 | 50 mg/ml | 150 mg | 3.0 ml |
| SR-bSt/150 | 6 | 150 mg/ml | 150 mg | 1.0 ml |
| SR-bSt/250 | 5 | 250 mg/ml | 150 mg | 0.6 ml |
| SR-bSt/50 | 6 | 50 mg/ml | 300 mg | 6.0 ml |

TABLE 1-continued

Experimental Design and Formulation Description.

| Formulation[a] | N | Somatotropin Concentration | Dose | Dose Volume |
|---|---|---|---|---|
| SR-bSt/150 | 6 | 150 mg/ml | 300 mg | 2.0 ml |
| SR-bSt/250 | 6 | 250 mg/ml | 300 mg | 1.2 ml |
| SR-bSt/50 | 6 | 50 mg/ml | 600 mg | 12 ml |
| SR-bSt/150 | 5 | 150 mg/ml | 600 mg | 4.0 ml |
| SR-bSt/250 | 5 | 250 mg/ml | 600 mg | 2.4 ml |
| Control[b] | 6 | — | — | — |

[a]All formulations involved lyophilized bSt dissolved in water for injection.
[b]Non-injected

TABLE 2

Serum bSt Concentration in Heifers by Bleeding Times after Injection of Various Concentrations and Doses of SR-bSt (Least Square Means (ng bSt/ml of serum)).

| Time | 150 mg SR-bSt 50 | 300 mg SR-bSt 50 | 600 mg SR-bSt 50 | 150 mg SR-bSt 150 | 300 mg SR-bSt 150 | 600 mg SR-bSt 150 | 150 mg SR-bSt 250 | 300 mg SR-bSt 250 | 600 mg SR-bSt 250 |
|---|---|---|---|---|---|---|---|---|---|
| 12 h | 69.4 | 190.0 | 300.4 | 39.3 | 69.5 | 199.9 | 24.3 | 89.7 | 101.5 |
| 24 h | 72.9 | 178.7 | 275.8 | 38.3 | 100.5 | 222.4 | 38.7 | 104.5 | 138.8 |
| 36 h | 30.1 | 109.6 | 205.5 | 27.3 | 66.4 | 215.2 | 26.0 | 61.3 | 145.8 |
| 48 h | 15.3 | 40.7 | 131.3 | 12.5 | 42.0 | 139.6 | 12.6 | 38.1 | 80.0 |
| 72 h | 4.2 | 12.8 | 55.6 | 8.6 | 18.2 | 56.1 | 6.2 | 19.2 | 44.2 |
| 96 h | $1.9^{ns}$ | 4.1 | 9.8 | 3.4 | 9.7 | 19.4 | 5.2 | 13.5 | 24.5 |
| 120 h | $2.6^{ns}$ | $2.6^{ns}$ | 2.7 | 3.2 | 6.6 | 10.3 | 3.7 | 8.2 | 17.2 |
| 144 h | $1.5^{ns}$ | $2.3^{ns}$ | $1.5^{ns}$ | $2.1^{ns}$ | 2.9 | 3.6 | $2.1^{ns}$ | 4.4 | 8.2 |
| 168 h | $1.1^{ns}$ | $1.2^{ns}$ | $1.1^{ns}$ | $1.2^{ns}$ | $1.6^{ns}$ | $2.8^{ns}$ | $1.2^{ns}$ | 3.0 | 6.3 |
| 192 h | $1.1^{ns}$ | $2.1^{ns}$ | $1.3^{ns}$ | $1.5^{ns}$ | $1.1^{ns}$ | $2.1^{ns}$ | $0.8^{ns}$ | $2.8^{ns}$ | 4.3 |
| 216 h | $1.3^{ns}$ | $1.1^{ns}$ | $1.0^{ns}$ | $1.5^{ns}$ | $1.2^{ns}$ | $1.4^{ns}$ | $1.4^{ns}$ | $2.5^{ns}$ | 3.3 |
| 240 h | $1.3^{ns}$ | $1.4^{ns}$ | $1.8^{ns}$ | $1.3^{ns}$ | $1.1^{ns}$ | $1.2^{ns}$ | $1.1^{ns}$ | $1.9^{ns}$ | $2.2^{ns}$ |
| 264 h | $1.9^{ns}$ | $1.6^{ns}$ | $1.9^{ns}$ | $2.0^{ns}$ | $2.0^{ns}$ | $1.6^{ns}$ | $1.5^{ns}$ | $2.4^{ns}$ | $2.3^{ns}$ |
| 288 h | $2.0^{ns}$ | $1.2^{ns}$ | $1.0^{ns}$ | $1.5^{ns}$ | $0.9^{ns}$ | $1.0^{ns}$ | $0.8^{ns}$ | $1.7^{ns}$ | $1.0^{ns}$ |
| 312 h | $1.3^{ns}$ | $1.8^{ns}$ | $0.9^{ns}$ | $2.1^{ns}$ | $1.7^{ns}$ | $1.0^{ns}$ | $0.7^{ns}$ | $2.1^{ns}$ | $0.9^{ns}$ |

[ns]Means with this superscript are not significantly (P > .05) different from over all control mean (1.8 ng bSt/ml serum). The control mean is the average concentration of bSt for all sampling times from 12 h through 312 h.

We claim:

1. A method for achieving prolonged release of greater than about 120 hours of a biologically active somatotropin into the circulatory system of an animal which comprises parenteral administration to the animal by subcutaneous or intramuscular injection of an aqueous bovine somatotropin composition consisting essentially of at least about 150 mg of a biologically active bovine somatotropin in water at a concentration of at least about 150 mg/ml.

2. The method of claim 1 wherein the aqueous bovine somatotropin composition consist essentially of at least about 300 mg of bovine somatotropin.

3. The method of claim 2 wherein the aqueous bovine somatotropin composition consists essentially of at least about 600 mg of bovine somatotropin.

4. The method of claim 1 wherein the aqueous bovine somatotropin composition has a concentration of at least about 250 mg/ml.

5. The method of claim 4 wherein the aqueous bovine somatotropin composition consists essentially of at least about 300 mg of bovine somatotropin.

6. The method of claim 5 wherein the aqueous bovine somatotropin composition consists essentially of at least about 600 mg of bovine somatotropin.

7. The method of claim 1 wherein the aqueous bovine somatotropin solution is void of absorption modifying agents.

8. A method for achieving prolonged release of greater than about 144 hours of a biologically active somatotropin into the circulatory system of an animal which comprises parenteral administration to the animal by subcutaneous or intramuscular injection of an aqueous bovine somatotropin composition consisting essentially of at least about 300 mg of a biologically active bovine somatotropin in water at a concentration of at least about 150 mg/ml.

9. The method of claim 8 wherein the aqueous bovine somatotropin composition consists essentially of at least about 600 mg of bovine somatotropin.

10. The method of claim 8 wherein the aqueous bovine somatotropin composition has a concentration of at least about 250 mg/ml.

11. The method of claim 10 wherein the aqueous bovine somatotropin composition consists essentially of at least about 600 mg of bovine somatotropin.

12. The method of claim 8 wherein the aqueous bovine somatotropin solution is void of absorption modifying agents.

13. A method for enhancing milk production or feed-to-milk conversion efficiency of a cow by effecting prolonged release of a biologically active somatotropin into the circulatory system of the cow for a period of at least about 120 hours by a single administration of the somatotropin to the cow which comprises parenteral administration to the cow of a syringeable aqueous bovine somatotropin solution having a concentration of at least 150 mg/ml whereby said solution provides the cow with at least a 150 mg dose of bovine somatotropin.

14. The method of claim 13 in which the composition is administered by subcutaneous or intramuscular injection.

15. The method of claim 13 in which milk production of the cow is enhanced for a period of at least about 7 days by a single administration.

16. A pharmaceutical composition comprising at least about 150 mg of a biologically active bovine somatotropin in water at a concentration of at least about 150 mg/ml to form a syringeable aqueous bovine somatotropin solution, said solution being void of absorption modifying agents and buffering agents.

17. The composition of claim 16 wherein said solution contains at least about 300 mg of a biologically active bovine somatotropin.

18. The composition of claim 17 wherein said solution contains at least about 600 mg of a biologically active bovine somatotropin.

19. A pharmaceutical composition comprising at least about 150 mg of a biologically active bovine somatotropin in water at a concentration of at least about 250 mg/ml to form a syringeable aqueous bovine somatotropin solution, said solution being void of absorption modifying agents.

20. The composition of claim 19 wherein said solution contains at least about 300 mg of a biologically active bovine somatotropin.

21. The composition of claim 19 wherein said solution contains at least about 600 mg of a biologically active bovine somatotropin.

\* \* \* \* \*